(12) United States Patent
Schmitz et al.

(10) Patent No.: US 9,708,304 B2
(45) Date of Patent: Jul. 18, 2017

(54) SALT POLYMORPH OF THIOXANTHENE-9-YLIDENE-1-METHYL PIPERIDINE ACID ADDITION SALTS AS ANTIMIGRAINE COMPOUNDS

(71) Applicant: BIOFRONTERA BIOSCIENCE GMBH, Leverkusen (DE)

(72) Inventors: Beate Schmitz, Köln (DE); Hermann Luebbert, Leverkusen (DE)

(73) Assignee: Biofrontera Bioscience GmbH, Leverkusen (DE)

( * ) Notice: Subject to any disclaimer, the term of this patent is extended or adjusted under 35 U.S.C. 154(b) by 0 days.

(21) Appl. No.: 14/765,176

(22) PCT Filed: Jan. 31, 2014

(86) PCT No.: PCT/EP2014/051863
§ 371 (c)(1),
(2) Date: Jul. 31, 2015

(87) PCT Pub. No.: WO2014/118307
PCT Pub. Date: Aug. 7, 2014

(65) Prior Publication Data
US 2015/0376168 A1    Dec. 31, 2015

(30) Foreign Application Priority Data
Feb. 1, 2013  (WO) ................. PCT/EP2013/052060

(51) Int. Cl.
| | | |
|---|---|---|
| C07D 211/00 | (2006.01) | |
| C07D 295/00 | (2006.01) | |
| C07D 409/00 | (2006.01) | |
| C07D 411/00 | (2006.01) | |
| C07D 417/00 | (2006.01) | |
| C07D 419/00 | (2006.01) | |
| A61K 31/445 | (2006.01) | |
| C07D 409/04 | (2006.01) | |

(52) U.S. Cl.
CPC ................. *C07D 409/04* (2013.01)

(58) Field of Classification Search
None
See application file for complete search history.

(56) References Cited

U.S. PATENT DOCUMENTS

2003/0166672 A1* 9/2003 Lubbert ............... C07D 401/04
514/297

FOREIGN PATENT DOCUMENTS

| EP | 1 306 376 A1 | 5/2003 |
| EP | 1 321 169 A1 | 6/2003 |

OTHER PUBLICATIONS

Ivanisevic, I. et al. Uses of X-Ray Powder Diffraction in the Pharmaceutical Industry. Pharmaceutical Formulation and Quality. Aug./Sep. 2011, p. 32.*
Thege, IK. et al. Transformation of Chloramphenicol Palmitate from Therapeutically Inactive Polymorph A to Active Polymorph B. Journal of Thermal Analysis. 1997, vol. 50, p. 867.*
Written Opinion and International Search Report from PCT/EP2013/051863 dated Feb. 26, 2014, 10 pages.
Written Opinion and International Search Report from PCT/EP2013/052060 dated Mar. 21, 2013, 10 pages.

* cited by examiner

*Primary Examiner* — Noble Jarrell
*Assistant Examiner* — Ben S Michelson
(74) *Attorney, Agent, or Firm* — Barnes & Thornburg LLP

(57) ABSTRACT

The present invention relates to novel crystal forms of 4-(6-ethoxy-1-methoxy-thioxanthene-9-ylidene)-1-methyl piperidine salts and 4-(6-ethoxy-1-hydroxy-thioxanthene-9-ylidene)-1-methyl piperidine salts; especially to novel crystal forms of 4-(6-ethoxy-1-methoxy-thioxanthene-9-ylidene)-1-methyl piperidine hydrochloride and 4-(6-ethoxy-1-hydroxy-thioxanthene-9-ylidene)-1-methyl piperidine hydrochloride as well as to the use of these salts for preventing or treating migraine or pulmonary hypertension.

15 Claims, 8 Drawing Sheets

SALT POLYMORPH OF THIOXANTHENE-9-YLIDENE-1-METHYL PIPERIDINE ACID ADDITION SALTS AS ANTIMIGRAINE COMPOUNDS

CROSS-REFERENCE TO RELATED APPLICATIONS

This application is a US National Phase filing of PCT/EP2014/051863, filed on Jan. 31, 2014, which claims priority of PCT/EP2013/052060, filed on Feb. 1, 2013, the entire disclosures of which are hereby expressly incorporated by reference.

The present invention relates to novel crystal forms of 4-(6-ethoxy-1-methoxy-thioxanthene-9-ylidene)-1-methyl piperidine salts and 4-(6-ethoxy-1-hydroxy-thioxanthene-9-ylidene)-1-methyl piperidine salts; especially to novel crystal forms of 4-(6-ethoxy-1-methoxy-thioxanthene-9-ylidene)-1-methyl piperidine hydrochloride and 4-(6-ethoxy-1-hydroxy-thioxanthene-9-ylidene)-1-methyl piperidine hydrochloride as well as to the use of these salts for preventing or treating migraine or pulmonary hypertension.

BACKGROUND OF THE INVENTION

Serotonin, a neurotransmitter with mixed and complex pharmacological characteristics, was first discovered in 1948, and subsequently has been the subject of substantial research. Serotonin, also referred to as 5-hydroxytryptamine (5-HT), acts both centrally and peripherally on discrete 5-HT receptors. Currently, fourteen subtypes of serotonin receptor are recognized and delineated into seven families, $5\text{-HT}_1$, to $5\text{-HT}_7$. Within the $5\text{-HT}_2$ family, $5\text{-HT}_{2A}$, $5\text{-HT}_{2B}$ and $5\text{-HT}_{2C}$ subtypes are known to exist. These subtypes share sequence homology and display similarities in their specificity for a wide range of ligands. Nomenclature and classification of 5-HT receptors have been reviewed (see Martin and Humphrey, Neuropharm. 1994, 33, 261-273 and Hoyer et al., Pharm. Rev. 1994, 46, 157-203).

The $5\text{-HT}_{2B}$ receptor, initially termed $5\text{-HT}_{2F}$, or serotonin receptor like (SRL), was first characterized in rat isolated stomach fundus (see Clineschmidt et al., J. Pharmacol. Exp. Ther, 1985, 235, 696-708; Cohen and Wittenauer, J. Cardiovasc. Pharmacol. 1987, 10, 176-181) and initially cloned from rat (see Foguet et al., EMBO 1992, 11, 3481-3487) followed by the cloning of the human $5\text{-HT}_{2B}$ receptor (see Schmuck et al., FEBS Lett. 1994, 342, 85-90; Kursar et al., Mol. Pharmacol. 1994, 46, 227-234). The closely related $5\text{-HT}_{2C}$ receptor, widely distributed in the human brain, was first characterized as a $5\text{-HT}_{1C}$ subtype (see Pazos et al., Eur. J. Pharmacol. 1984, 106, 539-546) and was subsequently recognized as belonging to the $5\text{-HT}_2$ receptor family (see Pritchett et al., EMBO J. 1988, 7, 4135-4.140).

Because of the similarities in the pharmacology of ligand interactions at $5\text{-HT}_{2B}$ and $5\text{-HT}_{2C}$ receptors, many of the therapeutic targets that have been proposed for $5\text{-HT}_{2C}$ receptor antagonists are also targets for $5\text{-HT}_{2B}$ receptor antagonists. Current evidence strongly supports a therapeutic role for $5\text{-HT}_{2B/2C}$ receptor antagonists in treating anxiety (e.g., generalized anxiety disorder, panic disorder and obsessive compulsive disorder), alcoholism and addiction to other drugs of abuse, depression, migraine, sleep disorders, feeding disorders (e.g., anorexia nervosa) and priapism. Additionally, current evidence strongly supports a therapeutic role for selective $5\text{-HT}_{2B}$ receptor antagonists that will offer distinct therapeutic advantages collectively in efficacy, rapidity of onset and absence of side effects. Such agents are expected to be useful in the treatment of hypertension, disorders of the gastrointestinal tract (e.g., irritable bowel syndrome, hypertonic lower esophageal sphincter, motility disorders), restenosis, asthma and obstructive airway disease, and prostatic hyperplasia (e.g., benign prostatic hyperplasia).

U.S. Pat. No. 3,275,640 describes generically substituted 1-hydrocarbyl-4-(9H-thioxanthene-9-ylidene)-piperidines and their preparation. It is also disclosed that the compounds may be used as therapeutic agents because of their antihistaminic and/or antiserotonin properties.

U.S. Pat. No. 3,557,287 relates to a combination preparation for use in the treatment of headaches of vascular origin containing as active constituents (a) a vasotonic lysergic acid selected from ergostine, ergotamine, dihydroergostine, dihydroergotamine, ergovaline, 5'-methylergoalanine; (b) caffeine; and (c) 9-(1-methyl-4-piperidylidene) thioxanthene (=1-methyl-4-(9H-thioxanthene-9-ylidene)-piperidine.

DE-A-22 56 392 discloses 4-(9H-thioxanthene-9-ylidene)-piperidine derivatives wherein the nitrogen atom of the piperidine ring is bonded to an alkyl radical substituted with cyano, —COR or —COOR. Sleep-inducing properties are attributed to these derivatives.

JP-A-61106573 refers to the use of substituted 4-(9H-thioxanthene-9-ylidene)-piperidines as pesticides.

Derivatives of 4-(thioxanthene-9-ylidene)-piperidine and 4-(selenoxanthene-9-ylidene)-piperidine useful in the treatment of various diseases have been described in US patent application 2003/0166672 A1, the content of which is herewith incorporated by reference in its entirety.

TECHNICAL PROBLEMS UNDERLYING THE PRESENT INVENTION AND THEIR SOLUTION

While pharmaceutical activity is the basic requirement for any given compound to be used as a medicament in therapy, there are several other requirements a pharmaceutically active compound has to fulfill before it will be approved as medicament for the treatment of humans or animals.

Such other requirements are connected to various parameters that are associated with the chemical and physical nature of the active compound itself. These parameters comprise, without limitation, the stability of the active compound under certain environmental conditions, its stability during the production process and the stability of the active compound in the final pharmaceutical preparation. In the event that the active compound is not stable in the final preparation of the medicament, the content of the active compound might decline over time so that a patient taking the medicament might receive an insufficient dose of the active compound. Furthermore, an instable active compound could degrade to breakdown products that might have unwanted side effects.

Therefore, it is desirable that an active compound has a high stability during the preparation process and in the final preparation of the medicament.

The inventors surprisingly found that stable salt polymorphs of 4-(thioxanthene-9-ylidene)-piperidine derivatives can be obtained by preparing acid addition salts under defined conditions. These stable salt polymorphs are well-suited for preparing stable pharmaceutical formulations having long-term stability.

The above-described objectives are solved and the advantages are achieved by the subject-matter of the enclosed independent claims. Preferred embodiments of the invention are included in the dependent claims as well as in the following description, examples and figures.

The above overview does not necessarily describe all problems solved by the present invention.

BRIEF DESCRIPTION OF THE INVENTION

In a first aspect the present invention relates to a salt polymorph of a 4-(6-ethoxy-1-methoxy-thioxanthene-9-ylidene)-1-methyl piperidine acid addition salt or a 4-(6-ethoxy-1-hydroxy-thioxanthene-9-ylidene)-1-methyl piperidine acid addition salt, wherein said salt polymorph is producible by a method comprising the steps of:
dissolving a 4-(6-ethoxy-1-methoxy-thioxanthene-9-ylidene)-1-methyl piperidine acid addition salt or a 4-(6-ethoxy-1-hydroxy-thioxanthene-9-ylidene)-1-methyl piperidine acid addition salt in a protic solvent and
removing said solvent at a temperature above 40° C.

In a second aspect the present invention relates to a salt polymorph of 4-(6-ethoxy-1-methoxy-thioxanthene-9-ylidene)-1-methyl piperidine hydrohalide characterized by an x-ray powder diffraction spectrum having peaks expressed as 2 theta at about [14.7, 18.2, 20.0, 20.9, 22.5, 22.7, 23.8, 25.1, 28.6, 44.7] degrees using XRPD radiation.

In a third aspect the present invention relates to a salt polymorph according to the first or second aspect or to 4-(6-ethoxy-1-methoxy-thioxanthene-9-ylidene)-1-methyl piperidine hydrochloride addition salt or to 4-(6-ethoxy-1-hydroxy-thioxanthene-9-ylidene)-1-methyl piperidine hydrochloride addition salt for use in preventing or treating migraine or pulmonary hypertension.

In a fourth aspect the present invention relates to a pharmaceutical composition comprising the salt polymorph according to the third aspect or the hydrochloride addition salt according to the third aspect and one or more pharmaceutical excipients or additives for use in preventing or treating migraine or pulmonary hypertension.

This summary of the invention does not necessarily describe all features of the present invention. Other embodiments will become apparent from a review of the ensuing detailed description.

DETAILED DESCRIPTION OF THE INVENTION

Definitions

Figure 1:
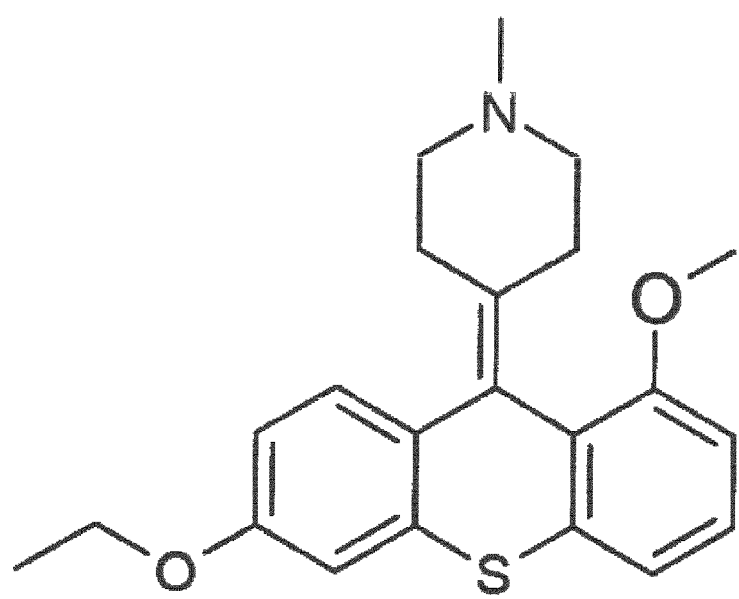
FIG. 1 shows the structural formula of 4-(6-ethoxy-1-methoxy-thioxanthene-9-ylidene)-1-methyl piperidine.

Before the present invention is described in detail below, it is to be understood that this invention is not limited to the particular methodology, protocols, and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art to which this invention belongs.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

Several documents (for example: patents, patent applications, scientific publications, manufacturer's specifications, instructions, GenBank Accession Number sequence submissions etc.) are cited throughout the text of this specification. Nothing herein is to be construed as an admission that the invention is not entitled to antedate such disclosure by virtue of prior invention. Some of the documents cited herein are characterized as being "incorporated by reference". In the event of a conflict between the definitions or teachings of such incorporated references and definitions or teachings recited in the present specification, the text of the present specification takes precedence.

The term "about" when used in connection with a numerical value is meant to encompass numerical values within a range having a lower limit that is 1% smaller than the indicated numerical value and having an upper limit that is 1% larger than the indicated numerical value.

As used herein, "treat", "treating" or "treatment" of a disease or disorder means accomplishing one or more of the following: (a) reducing the severity and/or duration of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

As used herein, "prevent", "preventing", "prevention", or "prophylaxis" of a disease or disorder means preventing that a disorder occurs in subject.

A "pharmaceutical composition" according to the invention may be present in the form of a composition, wherein the different active ingredients and diluents and/or carriers are admixed with each other, or may take the form of a combined preparation, where the active ingredients are present in partially or totally distinct form. An example for such a combination or combined preparation is a kit-of-parts.

A "therapeutic amount" or "therapeutically effective amount" is an amount of a therapeutic agent sufficient to achieve the intended purpose. The effective amount of a given therapeutic agent will vary with factors such as the nature of the agent, the route of administration, the size and species of the animal to receive the therapeutic agent, and the purpose of the administration. The effective amount in each individual case may be determined empirically by a skilled artisan according to established methods in the art.

As used herein, the terms "patient" or "subject" refer to any mammal or bird that may benefit from the compounds described herein. Preferably, a "subject" or "patient" is selected from the group consisting of laboratory animals (e.g. mouse or rat), domestic animals (including e.g. guinea pig, rabbit, chicken, turkey, pig, sheep, goat, camel, cow, horse, donkey, cat, or dog), or primates including chimpanzees and human beings. It is particularly preferred that the "subject" or "patient" is a human being.

"Pharmaceutically acceptable" means approved by a regulatory agency of the Federal or a state government or listed in the U.S. Pharmacopeia (United States Pharmacopeia-33/National Formulary-28 Reissue, published by the United States Pharmacopeial Convention, Inc., Rockville Md., publication date: April 2010) or other generally recognized pharmacopeia for use in animals, and more particularly in humans.

Embodiments of the Invention

The present invention will now be further described. In the following passages different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous, unless clearly indicated to the contrary.

In a first aspect the present invention is directed to a salt polymorph of a 4-(6-ethoxy-1-methoxy-thioxanthene-9-ylidene)-1-methyl piperidine acid addition salt or a 4-(6-ethoxy-1-hydroxy-thioxanthene-9-ylidene)-1-methyl piperidine acid addition salt, wherein said salt polymorph is producible by a method comprising the steps of:
  dissolving a 4-(6-ethoxy-1-methoxy-thioxanthene-9-ylidene)-1-methyl piperidine acid addition salt or a 4-(6-ethoxy-1-hydroxy-thioxanthene-9-ylidene)-1-methyl piperidine acid addition salt in a protic solvent and
  removing said solvent at a temperature above 40° C.

In a preferred embodiment of the first aspect the removing of said solvent in step (b) is carried out at a pressure above $5 \times 10^4$ Pa, preferably at a pressure above $6 \times 10^4$ Pa, more preferably at a pressure above $7 \times 10^4$ Pa, even more preferably at a pressure above $8 \times 10^4$ Pa, even more preferably at a pressure above $9 \times 10^4$ Pa, and most preferably at a pressure above $1 \times 10^5$ Pa.

In a preferred embodiment of the first aspect, the temperature in step (b) is in the range between 50° C. and 80° C., more preferably between 60° C. and 80° C., even more preferably between 65° C. and 75° C., and most preferably at about 70° C.

In a preferred embodiment of the first aspect the protic solvent is a polar protic solvent. It is further preferred that the polar protic solvent is an alcohol, preferably selected from the group consisting of methanol, ethanol, n-propanol, iso-propanol, n-butanol, sec-butanol, tert-butanol, n-pentanol, 2-methyl-butanol, 3-methyl-butanol, and hexanol. It is particulary preferred that the polar protic solvent is methanol.

In a second aspect the present invention is directed to a salt polymorph of 4-(6-ethoxy-1-methoxy-thioxanthene-9-ylidene)-1-methyl piperidine hydrohalide characterized by an x-ray powder diffraction spectrum having peaks expressed as 2 theta at about [14.7, 18.2, 20.0, 20.9, 22.5, 22.7, 23.8, 25.1, 28.6, 44.7] degrees using XRPD radiation.

In preferred embodiments of the first and second aspect, the salt is a hydrohalide, preferably a hydrochloride, hydrofluoride, hydrobromide, and hydroiodide. It is particulary preferred that the salt is a hydrochloride.

In further preferred embodiments of the first and second aspect, the salt polymorph has a differential scanning calorimetry melting temperature maximum of from about 242° C. to about 244° C., preferably from about 242.0° C. to about 244.0° C.

In further preferred embodiments of the first and second aspect, the salt polymorph has a differential scanning calorimetry heat of fusion of from about 90 to about 125 J/g.

In further preferred embodiments of the first and second aspect, the salt polymorph has a melting point of about 241° C., preferably of about 241.0° C.

In further preferred embodiments of the first and second aspect, the salt polymorph has major infrared absorbance peaks at about [775, 825, 1050, 1250, 1400-1600, 2400] cm$^{-1}$.

In a third aspect the present invention is directed to:
  a salt polymorph according to the first aspect;
  a salt polymorph according to the second aspect;
  4-(6-ethoxy-1-methoxy-thioxanthene-9-ylidene)-1-methyl piperidine hydrochloride addition salt; or
  4-(6-ethoxy-1-hydroxy-thioxanthene-9-ylidene)-1-methyl piperidine hydrochloride addition salt
for use in preventing or treating migraine or pulmonary hypertension.

The third aspect of the present invention can alternatively be worded as follows: In a third aspect the present invention is directed to a method for treating migraine or pulmonary hypertension, comprising the step: administering a therapeutic amount of
  a salt polymorph according to the first aspect;
  a salt polymorph according to the second aspect;
  4-(6-ethoxy-1-methoxy-thioxanthene-9-ylidene)-1-methyl piperidine hydrochloride addition salt; or
  4-(6-ethoxy-1-hydroxy-thioxanthene-9-ylidene)-1-methyl piperidine hydrochloride addition salt
to a subject in need thereof.

In an especially preferred embodiment of the third aspect, the present invention is directed to:
  a salt polymorph according to the first aspect;
  a salt polymorph according to the second aspect;

4-(6-ethoxy-1-methoxy-thioxanthene-9-ylidene)-1-methyl piperidine hydrochloride addition salt; or 4-(6-ethoxy-1-hydroxy-thioxanthene-9-ylidene)-1-methyl piperidine hydrochloride addition salt for use in preventing or treating migraine.

This especially preferred embodiment of the third aspect can alternatively be worded as follows: the present invention is directed to a method for treating migraine, comprising the step: administering a therapeutic amount of a salt polymorph according to the first aspect;

a salt polymorph according to the second aspect;

4-(6-ethoxy-1-methoxy-thioxanthene-9-ylidene)-1-methyl piperidine hydrochloride addition salt; or 4-(6-ethoxy-1-hydroxy-thioxanthene-9-ylidene)-1-methyl piperidine hydrochloride addition salt to a subject in need thereof.

In a fourth aspect the present invention is directed to a pharmaceutical composition comprising a salt polymorph according to the third aspect [i.e. a salt polymorph according to the first aspect or a salt polymorph according to the second aspect] or a hydrochloride addition salt according to the third aspect [i.e. 4-(6-ethoxy-1-methoxy-thioxanthene-9-ylidene)-1-methyl piperidine hydrochloride addition salt or 4-(6-ethoxy-1-hydroxy-thioxanthene-9-ylidene)-1-methyl piperidine hydrochloride addition salt] and one or more pharmaceutical excipients or additives for use in preventing or treating migraine or pulmonary hypertension.

In a preferred embodiment of the fourth aspect, the pharmaceutical composition is for use in oral, rectal, intragastrical, intracranial and parenteral administration.

In a further preferred embodiment of the fourth aspect, the parenteral administration is selected from the group consisting of intravenous, intramuscular, intranasal, intradermal, and subcutaneous administration.

In applying the compounds of this invention to treatment of the above conditions, administration of the active compound and salts described herein can be via any of the accepted modes of administration, including oral, parenteral and otherwise systemic route of administration. Any pharmaceutically acceptable mode of administration can be used, including solid, semi-solid or liquid dosage forms, such as, for example, tablets, suppositories, pills, capsules, powders, liquids, suspensions, or the like, preferably in unit dosage forms suitable for single administration of precise dosages, or in sustained or controlled release dosage forms for the prolonged administration of the compound at a predetermined rate. The compositions will typically include a conventional pharmaceutical carrier or excipient and at least one of the compounds of the present invention or the pharmaceutically acceptable salts thereof and, in addition, may include other medicinal agents, pharmaceutical agents, carriers, adjuvants, etc.

The amount of one of the compounds and salts of the present invention administered will of course, be dependent on the subject being treated, the severity of the affliction, the manner of administration and the judgment of the prescribing physician. However, an effective dose for oral, parenteral and otherwise systemic routes of administration is in the range of 0.01-20 mg/kg/day, preferably 0.1-10 mg/kg/day. For an average 70 kg human, this would amount to 0.7-1400 mg per day, or preferably 7-700 mg/day.

One of ordinary skill in the art of treating such diseases will be able, without undue experimentation and in reliance upon personal knowledge and the disclosure of this application, to ascertain a therapeutically effective amount of one of the inventive piperidine compounds for a given disease.

For solid compositions, conventional non-toxic solid carriers include, for example, pharmaceutical grades of mannitol, lactose, cellulose, cellulose derivatives, sodium crosscarmellose, starch, magnesium stearate, sodium saccharin, talcum, glucose, sucrose, magnesium carbonate, and the like may be used. The active compound as defined above may be formulated as suppositories using, for example, polyalkylene glycols, e.g PEG (polyethyleneglycol) or PEG derivatives, acetylated triglycerides and the like, as the carrier. Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, sorbitan monolaurate, triethanolamine oleate, etc. The composition or formulation to be administered will, in any event, contain a quantity of the active compound(s) in an amount effective to alleviate the symptoms of the subject being treated.

Dosage forms or compositions containing one of the compounds and salts described herein in the range of 0.25 to 95% by weight with the balance made up from non-toxic carrier may be prepared.

For oral administration, a pharmaceutically acceptable non-toxic composition is formed by the incorporation of any of the normally employed excipients, such as, for example pharmaceutical grades of mannitol, lactose, cellulose, cellulose derivatives, sodium crosscarmellose, starch, magnesium stearate, sodium saccharin, talcum, glucose, sucrose, magnesium, carbonate, and the like. Such compositions take the form of solutions, suspensions, tablets, pills, capsules, powders, sustained release formulations and the like. Such compositions may contain 1 to 95% by weight of one of the compounds of the present invention, more preferably 2 to 50% by weight, most preferably 5 to 8% by weight.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, triethanolamine sodium acetate, etc.

Transdermal or "pulsed" transdermal administration may be supported by cremes, gels, dispersions and the like.

A more recently devised approach for parenteral administration employs the implantation of a slow-release or sustained-release system, such that a constant level of dosage is maintained (see, e.g., U.S. Pat. No. 3,710,795).

The percentage of active compounds contained in such parental compositions is highly dependent on the specific nature thereof, as well as the activity of the compound and the needs of the subject. However, percentages of one of the inventive compounds of 0.1 to 10% by weight in solution are employable, and will be higher if the composition is a solid which will be subsequently diluted to the above percentages.

Preferably the composition will comprise 0.2 to 2% by weight of one of the compounds of the invention in solution.

The compositions of the present invention may also be formulated for administration in any convenient way by analogy with other topical compositions adapted for use in mammals. These compositions may be presented for use in any conventional manner with the aid of any of a wide variety of pharmaceutical carriers or vehicles. For such topical administration, a pharmaceutically acceptable non-toxic formulation can take the form of semisolid, liquid, or solid, such as, for example, gels, creams, lotions, solutions, suspensions, ointments, powders, or the like. As an example, the active component may be formulated into a syrup or gel using ethanol, propylene glycol, propylene carbonate, polyethylene glycols, diisopropyl adipate, glycerol, water, etc., with appropriate gelling agents, such as Carbomers, Klucels, etc. If desired, the formulation may also contain minor amounts of non-toxic auxiliary substances such as preservatives, antioxidants, pH buffering agents, surface active agents, and the like. Actual methods of preparing such dosage forms are known, or will be apparent, to those skilled in the art; for example, see Remington's Pharmaceutical Sciences, Mack Publishing Company, Easton, Pa., 19th Edition, 1995.

Preferably the pharmaceutical composition is administered in a single unit dosage form for continuous treatment or in a single unit dosage form ad libitum when relief of symptoms is specifically required.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used but some experimental errors and deviations should be accounted for. Unless indicated otherwise, molecular weight is average molecular weight, temperature is in degrees centigrade, and pressure is at or near atmospheric.

Example 1

Crystallization Experiments 4-(6-ethoxy-1-methoxy-thioxanthene-9-ylidene)-1-methyl piperidine free base purified by column chromatography was used in the following tests. Evaporation of the solvents left the material as light brown glass-like semisolid with 93% assay by titrimetry.

For the calculation of the amount of 4-(6-ethoxy-1-methoxy-thioxanthene-9-ylidene)-1-methyl piperidine it was taken as 100% material. Thus, there was always slight excess of the acid over 4-(6-ethoxy-1-methoxy-thioxanthene-9-ylidene)-1-methyl piperidine in the prepared solutions.

The results of the tests are summarized in Table 1.
1.1. Salt Formation of 4-(6-ethoxy-1-methoxy-thioxanthene-9-ylidene)-1-methyl piperidine with Organic Acids
1.1.1. Malic Acid in Isopropyl Alcohol The stock solution of 4-(6-ethoxy-1-methoxy-thioxanthene-9-ylidene)-1-methyl piperidine (S1) was prepared by dissolving 4-(6-ethoxy-1-methoxy-thioxanthene-9-ylidene)-1-methyl piperidine (1 g; 2.72 mmol) in i-PrOH (10 g).

The solution of malic acid (400 mg; c=1 mmol/g; 0.4 mmol) in i-PrOH was added to a solution of 4-(6-ethoxy-1-methoxy-thioxanthene-9-ylidene)-1-methyl piperidine in i-PrOH (1.47 g; 0.4 mmol) at +50° C. Upon cooling oily layer separated. Some i-PrOH (2 ml) was added to create homogeneous solution, which was then cooled slowly to +4° C., then overnight at −20° C. By morning some of the material had solidified. Attempt to separate the solids by filtration was unsuccesful (solids liquified-melted).
1.1.2. Tartaric Acid in Isopropyl Alcohol The solution of tartaric acid in i-PrOH (400 mg; c=1 mmol/g; 0.4 mmol) was added to a solution of 4-(6-ethoxy-1-methoxy-thioxanthene-9-ylidene)-1-methyl piperidine in i-PrOH (S1) (1.47 g; 0.4 mmol) at +50° C. Upon cooling oily layer separated. i-PrOH (2 ml) was added to dissolve it and the solution was heated until formation of clear solution (+50° C.). Upon cooling oily layer separated. The mixture was heated to +50° C., diluted with water (0.5 ml), cooled slowly to +4° C., then overnight at −20° C. By morning small amount of precipitate had formed. Attempt to separate the precipitate by filtration was unsuccessful (solids liquified-melted).
1.1.3. Citric Acid in Aqueous Isopropyl Alcohol The aqueous solution of citric acid (200 mg; c=2 mmol/g; 0.4 mmol) was added to a solution of 4-(6-ethoxy-1-methoxy-thioxanthene-9-ylidene)-1-methyl piperidine in i-PrOH (S1) (1.47 g; 0.4 mmol) at RT. By addition of about half of acid the mixture became cloudy. After addition of all citric acid clear solution formed again. The mixture was cooled slowly to +4° C., no precipitate formation. The mixture was concentrated on vacuum evaporator. The residue was dissolved in water (1.5 ml) and cooled to +4° C. for 4 hours. No precipitate formation.
1.1.4. 4-Methoxybenzoic Acid in Isopropyl Alcohol 4-Methoxybenzoic acid (304 mg; 2 mmol) was added in portions to a solution of 4-(6-ethoxy-1-methoxy-thioxanthene-9-ylidene)-1-methyl piperidine (734 mg, 2 mmol) in i-PrOH (4 ml). The clear solution was stirred at +4° C. for 2 hours. Then water (3 ml) was added dropwise. The resulting cloudy solution was stirred at +4° C. for 4 hours. No precipitate formation.
1.1.5. Acetic Acid in Isopropyl Alcohol Acetic acid (120 mg; 2 mmol) was added to a solution of 4-(6-ethoxy-1-methoxy-thioxanthene-9-ylidene)-1-methyl piperidine (734 mg, 2 mmol) in i-PrOH (4 ml). The clear solution was stirred at +4° C. for 4 hours, then concentrated on vacuum evaporator, diluted with THF (4 ml), stirred at +4° C. for 2 hours, diluted with water (4 ml) and stirred at +4° C. for 2 hours. No precipitate formation.
1.1.6. Citric Acid in Aqueous Methanol The solution of citric acid (600 mg; c=1.5 mmol/g; 1 mmol) in water was added to a solution of 4-(6-ethoxy-1-methoxy-thioxanthene-9-ylidene)-1-methyl piperidine in MeOH (2 g; c=0.5 mmol/g; 1 mmol) at RT. The clear solution was stirred at +4° C. for 20 hours. No precipitate formation.
1.1.7. Malic Acid in Aqueous Methanol The solution of malic acid (500 mg; c=2 mmol/g; 1 mmol) in water was added to a solution of 4-(6-ethoxy-1-methoxy-thioxanthene-9-ylidene)-1-methyl piperidine in MeOH (2 g; c=0.5 mmol/g; 1 mmol) at RT. The clear solution was stirred at +4° C. for 20 hours. No precipitate formation.
1.1.8. Tartaric Acid in Aqueous Methanol The solution of tartaric acid (500 mg; c=2 mmol/g; 1 mmol) in water was added to a solution of 4-(6-ethoxy-1-methoxy-thioxanthene-9-ylidene)-1-methyl piperidine in MeOH (2 g; c=0.5 mmol/g; 1 mmol) at RT. The clear solution was stirred at +4 for 20 hours. No precipitate formation.

1.1.9. Malic Acid in Methanol

Malic acid (134 mg; 1 mmol) was added to a solution of 4-(6-ethoxy-1-methoxy-thioxanthene-9-ylidene)-1-methyl piperidine in MeOH (2 g; c=0.5 mmol/g; 1 mmol) at RT. The clear solution was stirred at +4° C. for 2 hours, then at −20° C. for 20 hours. No precipitate formation.

1.1.10. Tartaric Acid in EtOH/i-PrOH

Tartaric acid (150 mg; 1 mmol) was added to a solution of 4-(6-ethoxy-1-methoxy-thioxanthene-9-ylidene)-1-methyl piperidine in MeOH (2 g; c=0.5 mmol/g; 1 mmol) at RT. The solution was stirred at +4° C. for 2 hours, diluted with acetone (2 ml), still clear solution. The solvents were removed on vacuum evaporator, the residue was dissolved in methanol (2 ml), diluted with i-PrOH (4 ml) and concentrated again. The residue was dissolved in boiling i-PrOH, diluted with absolute EtOH and cooled slowly to RT. Yellow precipitate of uneven consistency formed. Yield 274 mg. Repeated crystallization attempt using only EtOH (95%) gave no precipitate.

1.1.11. Malic Acid in Toluene

Malic acid (134 mg; 1 mmol) was added to a solution of 4-(6-ethoxy-1-methoxy-thioxanthene-9-ylidene)-1-methyl piperidine in toluene (2 g; c=0.5 mmol/g; 1 mmol) at RT. The clear solution was left at +4° C. for 72 hours. No precipitate formation.

1.1.12. Mandelic Acid in Toluene

Mandelic acid (152 mg; 1 mmol) was added to a solution of 4-(6-ethoxy-1-methoxy-thioxanthene-9-ylidene)-1-methyl piperidine in toluene (2 g; c=0.5 mmol/g; 1 mmol) at RT. The clear solution was left at +4° C. for 72 hours. 175 mg of large light yellow crystals were obtained.

1.1.13. 4-Methoxybenzoic Acid in Toluene

4-Methoxybenzoic acid (152 mg; 1 mmol) was added to a solution of 4-(6-ethoxy-1-methoxy-thioxanthene-9-ylidene)-1-methyl piperidine in toluene (2 g; c=0.5 mmol/g; 1 mmol) at RT. The clear solution was left at +4° C. for 72 hours. No precipitate formation.

1.1.14. Salicylic Acid in Toluene

Salicylic acid (138 mg; 1 mmol) was added to a solution of 4-(6-ethoxy-1-methoxy-thioxanthene-9-ylidene)-1-methyl piperidine in toluene (2 g; c=0.5 mmol/g; 1 mmol) at RT. The clear solution was left at +4° C. for 72 hours. No precipitate formation.

1.1.15. Acetic Acid in Toluene

Acetic acid (60 mg; 1 mmol) was added to a solution of 4-(6-ethoxy-1-methoxy-thioxanthene-9-ylidene)-1-methyl piperidine in toluene (2 g; c=0.5 mmol/g; 1 mmol) at RT. The clear solution was left at +4° C. for 72 hours. No precipitate formation.

1.1.16. Malic Acid in Acetone

Malic acid (134 mg; 1 mmol) was added to a solution of 4-(6-ethoxy-1-methoxy-thioxanthene-9-ylidene)-1-methyl piperidine in acetone (2 g; c=0.5 mmol/g; 1 mmol) at RT. The clear solution was left at +4° C. for 72 hours. No precipitate formation.

1.1.17. Mandelic Acid in Acetone

Mandelic acid (152 mg, 1 mmol) was used to a solution of 4-(6-ethoxy-1-methoxy-thioxanthene-9-ylidene)-1-methyl piperidine in acetone (2 g; c=0.5 mmol/g; 1 mmol) at RT. The clear solution was left at +4° C. for 72 hours. No precipitate formation.

1.1.18. 4-Methoxybenzoic Acid in Toluene

4-Methoxybenzoic acid (152 mg; 1 mmol) was added to a solution of 4-(6-ethoxy-1-methoxy-thioxanthene-9-ylidene)-1-methyl piperidine in acetone (2 g; c=0.5 mmol/g; 1 mmol) at RT. The clear solution was left at +4° C. for 72 hours. No precipitate formation.

1.1.19. Salicylic Acid in Acetone

Salicylic acid (138 mg; 1 mmol) was added to a solution of 4-(6-ethoxy-1-methoxy-thioxanthene-9-ylidene)-1-methyl piperidine in acetone (2 g; c=0.5 mmol/g; 1 mmol) at RT. The clear solution was left at +4° C. for 72 hours. No precipitate formation.

1.1.20. n-Decanoic Acid in i-Butyl Methyl Ether n-Decanoic acid (172 mg; 1 mmol) was added to a solution of 4-(6-ethoxy-1-methoxy-thioxanthene-9-ylidene)-1-methyl piperidine in t-butyl methyl ether (2 g; c=0.5 mmol/g; 1 mmol) at RT. The clear solution was left at +4° C. for 24 h. No precipitate formation.

1.1.21. n-Decanoic Acid in Methanol n-Decanoic (172 mg; 1 mmol) was added to a solution of 4-(6-ethoxy-1-methoxy-thioxanthene-9-ylidene)-1-methyl piperidine in methanol (2 g; c=0.5 mmol/g; 1 mmol) at RT. The clear solution was left at +4° C. for 24 h. No precipitate formation.

1.2. Salt Formation of 4-(6-ethoxy-1-methoxy-thioxanthene-9-ylidene)-1-methyl piperidine with HCl 1.2.1. HCl in Methanol The solution of dry HCl in i-PrOH (~0.3 ml; ~10%) was added dropwise to a solution of 4-(6-ethoxy-1-methoxy-thioxanthene-9-ylidene)-1-methyl piperidine (367 mg; 1 mmol) in MeOH (2 ml) at RT. The mixture was stirred for 1 hour at RT, then for 30 min at +4° C. (icebath) and filtered. Yield 110 mg of white crystals. The filtrate was pink coloured.

1.2.2. HCl in Ethanol

The solution of dry HCl in i-PrOH (~0.6 ml; ~10%) was added dropwise to a solution of 4-(6-ethoxy-1-methoxy-thioxanthene-9-ylidene)-1-methyl piperidine (734 mg; 2 mmol) in EtOH (4 ml; 95%) at RT. The mixture was stirred for 20 hours at RT. The precipitate was filtered off and washed with i-PrOH (2 ml) and Et$_2$O (1 ml). Yield 508 mg of white crystals.

1.2.3. HCl in Isopropyl Alcohol

The solution of dry HCl in i-PrOH (~0.6 ml; ~10%) was added dropwise to a solution of 4-(6-ethoxy-1-methoxy-thioxanthene-9-ylidene)-1-methyl piperidine (734 mg; 2 mmol) in i-PrOH (4 ml) at RT. The mixture was stirred for 20 hours at RT. The resulting precipitate was very fine, filtration was not attempted.

1.2.4. HCl in Tetrahydrofuran

The solution of dry HCl in i-PrOH (~0.6 ml; ~10%) was added dropwise to a solution of 4-(6-ethoxy-1-methoxy-thioxanthene-9-ylidene)-1-methyl piperidine (734 mg; 2 mmol) in THF (4 ml) at RT. The mixture was stirred for 4 hours at +4° C. The precipitate was filtered off and washed with Et$_2$O (2 ml). Yield 520 mg of light-brown crystals. The crystals were finer than those from methanol or ethanol.

1.2.5. Salt Formation of 4-(6-ethoxy-1-methoxy-thioxanthene-9-ylidene)-1-methyl piperidine with HCl in Acetone The solution of dry HCl in i-PrOH (~0.6 ml; ~10%) was added dropwise to a solution of 4-(6-ethoxy-1-methoxy-thioxanthene-9-ylidene)-1-methyl piperidine (734 mg; 2 mmol) in acetone (4 ml) at RT. The mixture was stirred overnight at +4° C. and filtered (very fine crystals). The precipitate was washed with Et$_2$O (2*2 ml). Yield 543 mg of light-brown crystals.

TABLE 1

Results of the salt-screening tests

| | | Solvent | | | | | | | | | |
|---|---|---|---|---|---|---|---|---|---|---|---|
| No. | Acid | MeOH | Aqueous MeOH | EtOH | EtOH/ i-PrOH | i-PrOH | Aqueous i-PrOH | Tol- uene | Ace- tone | THF | MTBE |
| 1 | HCl | + | | + | | + | | | + | + | |
| 2 | malic | − | − | | | − | | − | − | | |
| 3 | mandelic | | | | | | | + | − | | |
| 4 | p-methoxy benzoic | | | | | − | | − | − | | |
| 5 | salicylic | | | | | | − | − | − | | |
| 6 | citric | | − | | | | | − | | | |
| 7 | tartaric | | − | | + | − | | | | | |
| 8 | n-decanoic | − | | | | | | | | | − |
| 9 | acetic | | | | | − | | − | | | |

+ precipitate
− no precipitate

The tartrate salt (see section 1.1.10) and mandelate salt (see section 1.1.12) were analyzed by NMR (results are not shown). In the tartrate salt the ratio of 4-(6-ethoxy-1-methoxy-thioxanthene-9-ylidene)-1-methyl piperidine and tartaric acid is close to 1:1 while in the mandelate salt about twofold excess of mandelic acid can be seen.

The precipitate obtained using tartaric acid had the expected molar ratio. However, the precipitate exhibited uneven consistency. This makes the use of tartaric acid problematic.

Although nice looking crystals were obtained with mandelic acid, it would be difficult to use mandelic acid because of the poor observed stoichiometry of the salt.

Purity of the hydrochloride salts obtained with MeOH, EtOH, THF, and acetone was evaluated using HPLC by determining the peak area percentages at 235 nm and 237 nm. The area of the main peak in the HPLC analysis was in a range between 99.09% and 99.79% at 235 nm and between 99.14 and 99.79% at 237 nm (data not shown). The results demonstrate the excellent purity of the hydrochloride addition salts.

The yields obtained in the crystallization with HCl were 27%, 63%, 64% and 67% when using MeOH, EtOH, THF, and acetone, respectively, as solvent.

Thus, the best purification effect was obtained from methanol but the yield was low. A better combination of purity and yield was obtained from ethanol. THF and acetone gave coloured precipitates. The purity of the THF and acetone salts was lower and the yield was not significantly better compared to ethanol.

Example 2

Polymorphic Screening

The aim of this study was to investigate whether the hydrochloric salt of 4-(6-ethoxy-1-methoxy-thioxanthene-9-ylidene)-1-methyl piperidine can form other more crystalline forms than the one observed in pilot batches. In the event that other forms are identified, it was another aim to determine stability as compared to the form of the pilot material.

2.1 First Evaluation

The starting material was prepared from oxalate with a low purity by adding the oxalate salt to MTBE/NaOH mix to wash out the oxalic acid. HCl was added in methanol/isopropanol solution. The transfer/crystallisation to the HCl salt had a good purifying effect. The starting material was analysed as a reference, sample no 1.

The following systems were tested:

1. 4-(6-ethoxy-1-methoxy-thioxanthene-9-ylidene)-1-methyl piperidine hydrochloride—starting material used for crystallisations (2 g).
2. 4-(6-ethoxy-1-methoxy-thioxanthene-9-ylidene)-1-methyl piperidine hydrochloride (2 g) was dissolved in 20 ml of MeOH at room temperature and evaporated to dryness on ice bath at 8 mbar (~2 g).
3. 4-(6-ethoxy-1-methoxy-thioxanthene-9-ylidene)-1-methyl piperidine hydrochloride (2 g) was dissolved in 20 ml of MeOH at room temperature and evaporated to dryness at 70° C. (~2 g).
4. 4-(6-ethoxy-1-methoxy-thioxanthene 9-ylidene)-1-methyl piperidine hydrochloride (2 g) was dissolved in 4 ml of MeOH at 53° C., thereafter 9 ml of warm MTBE was added and the obtained solution cooled to 10° C. Crystals formed a crust on glass wall. The solvent was decanted and the flask washed with MTBE. By drying the flask under vacuum the crust broke loose very easily (1.9 g).
5. 4-(6-ethoxy-1-methoxy-thioxanthene-9-ylidene)-1-methyl piperidine hydrochloride (2 g) was dissolved in 4 ml of MeOH at 53° C., thereafter 9 ml of warm EtOAc was added and the obtained solution cooled to 10° C. Fine crystals formed very slowly. 1.3 g of crystals was obtained.
6. 4-(6-ethoxy-1-methoxy-thioxanthene-9-ylidene)-1-methyl piperidine hydrochloride (3 g) was dissolved in 6 ml of MeOH at 53° C., thereafter 12 ml of warm acetone was added and the obtained solution cooled to 10° C. No crystals were formed. 1.3 g of crystals was obtained by cooling to −20° C. Formation of crystals was slow.

No crystals were obtained by dissolving 2 g of 4-(6-ethoxy-1-methoxy-thioxanthene-9-ylidene)-1-methyl piperidine hydrochloride in 4 ml of MeOH and by adding 6 ml of toluene.

The samples were analyzed using IR, DSC and XRPD.

TABLE 2

Results from First Evaluation of Polymorphic Screening

Figure 2:
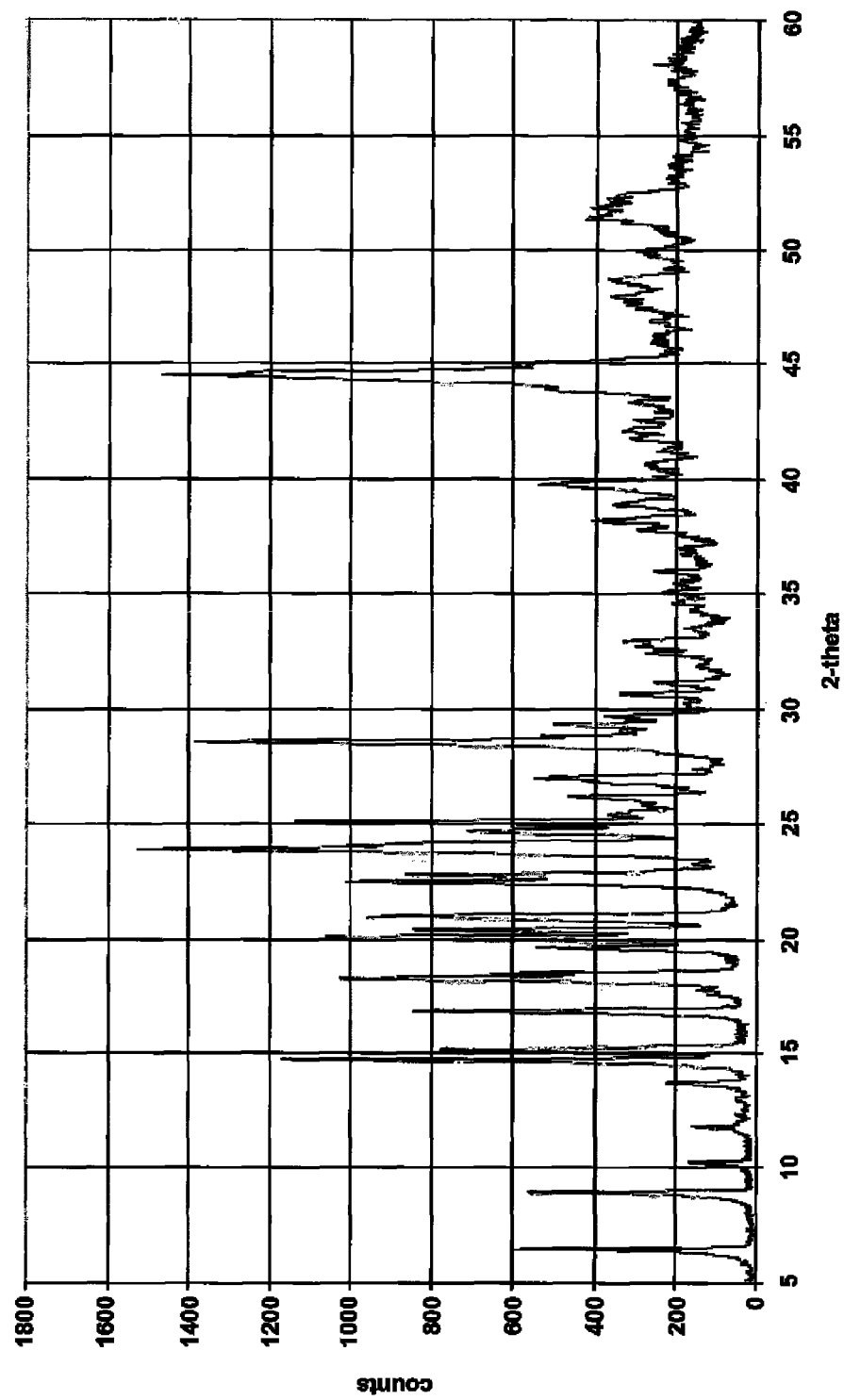
FIG. 2 shows an x-ray powder diffraction spectrum of the starting material used for crystallizations, i.e. 4-(6-ethoxy-1-methoxy-thioxanthene-9-ylidene)-1-methyl piperidine hydrochloride.
Figure 5:
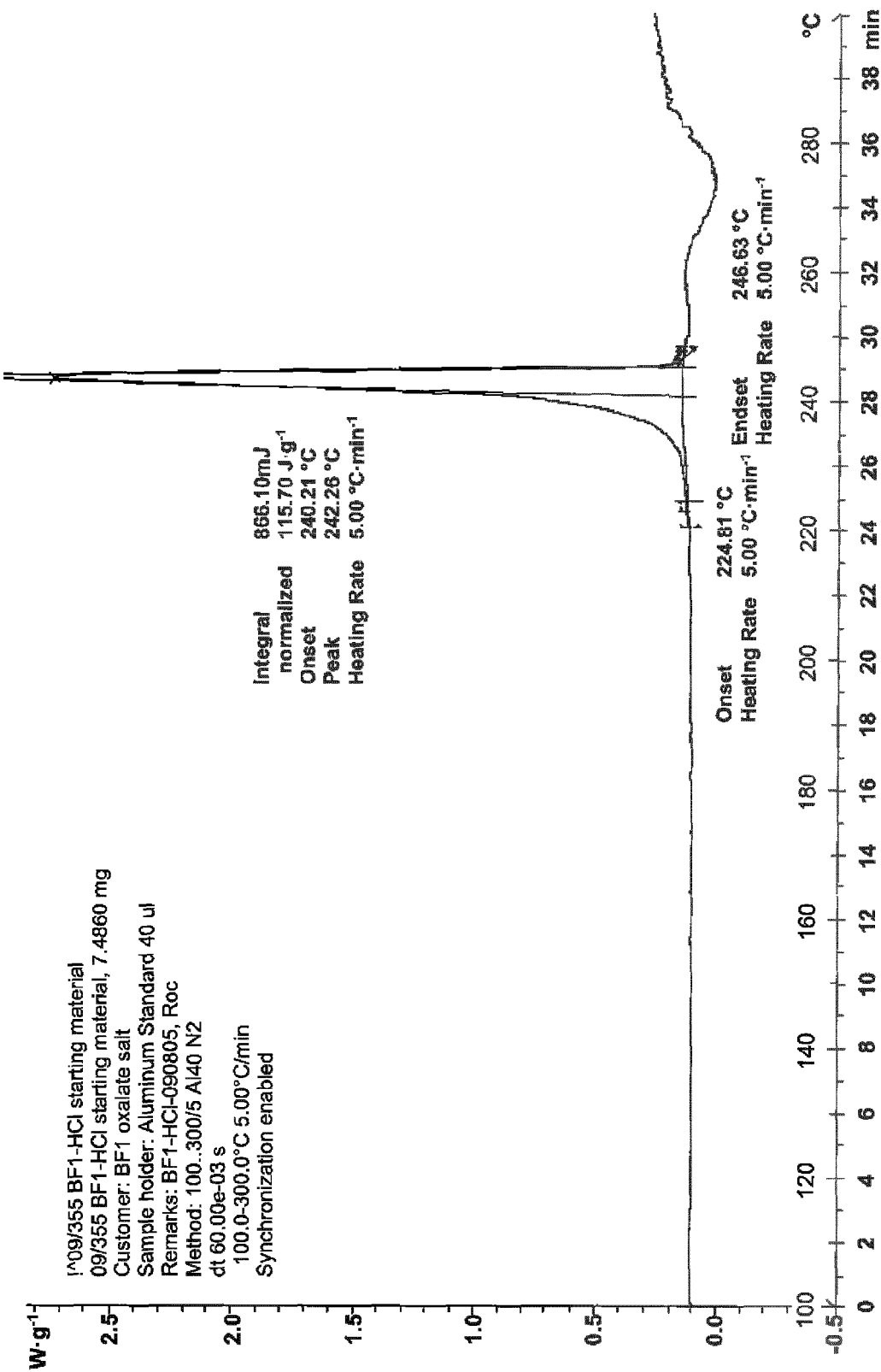
FIG. 5 shows a differential scanning calorimetry (DSC) analysis of the starting material used for crystallizations, i.e. 4-(6-ethoxy-1-methoxy-thioxanthene-9-ylidene)-1-methyl piperidine hydrochloride.

| Sample Id | Method/Solvent | DSC Comparable with reference | XRPD Comparable with reference | Comment |
|---|---|---|---|---|
| 1 | Starting material | NA | NA | see FIG. 2 and FIG. 5 |

TABLE 2-continued

Results from First Evaluation of Polymorphic Screening

Figure 3:
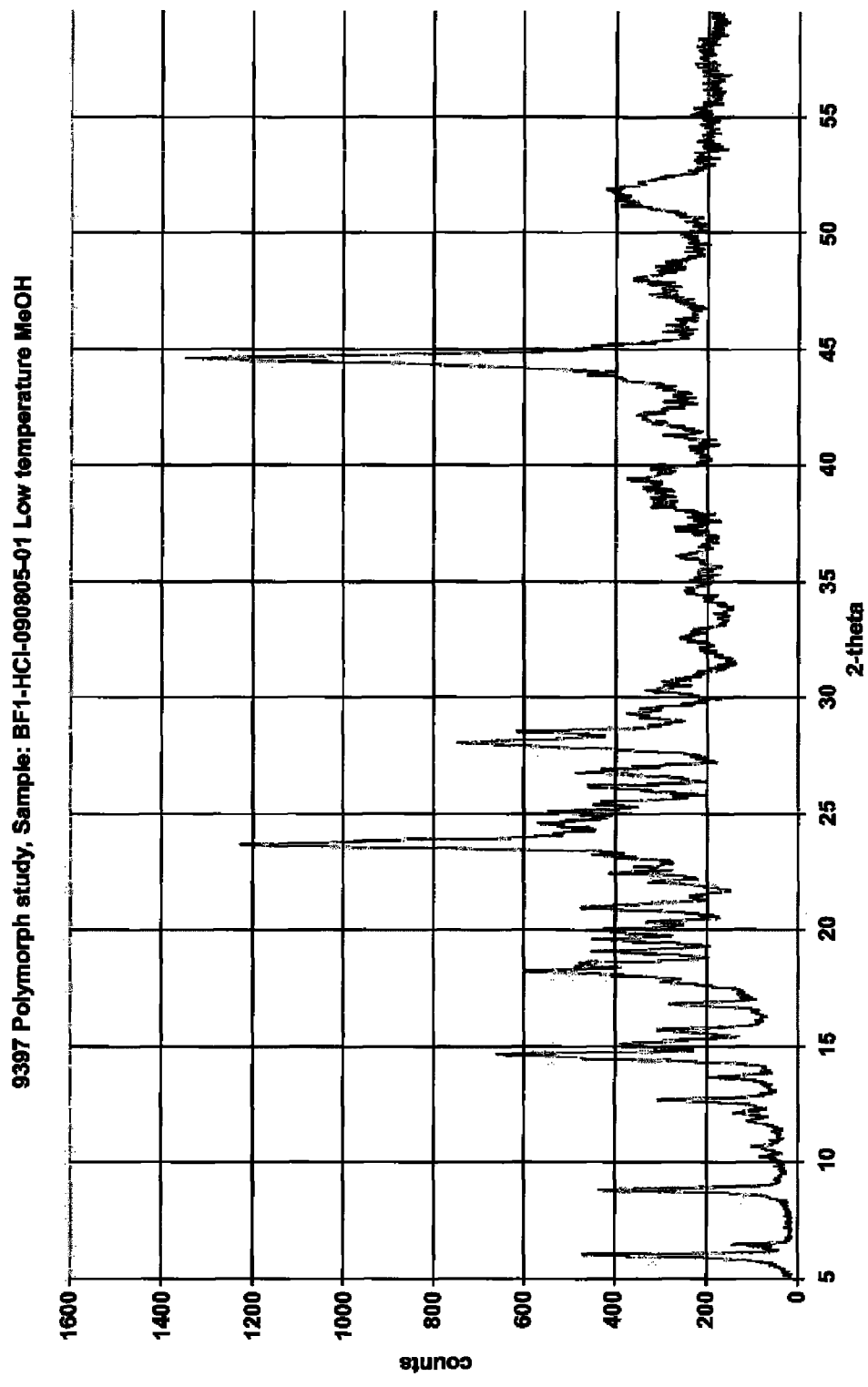
FIG. 3 shows an x-ray powder diffraction spectrum of crystals of 4-(6-ethoxy-1-methoxy-thioxanthene-9-ylidene)-1-methyl piperidine hydrochloride that were obtained by dissolving the starting material in MeOH and low temperature evaporation under reduced pressure.
Figure 6:
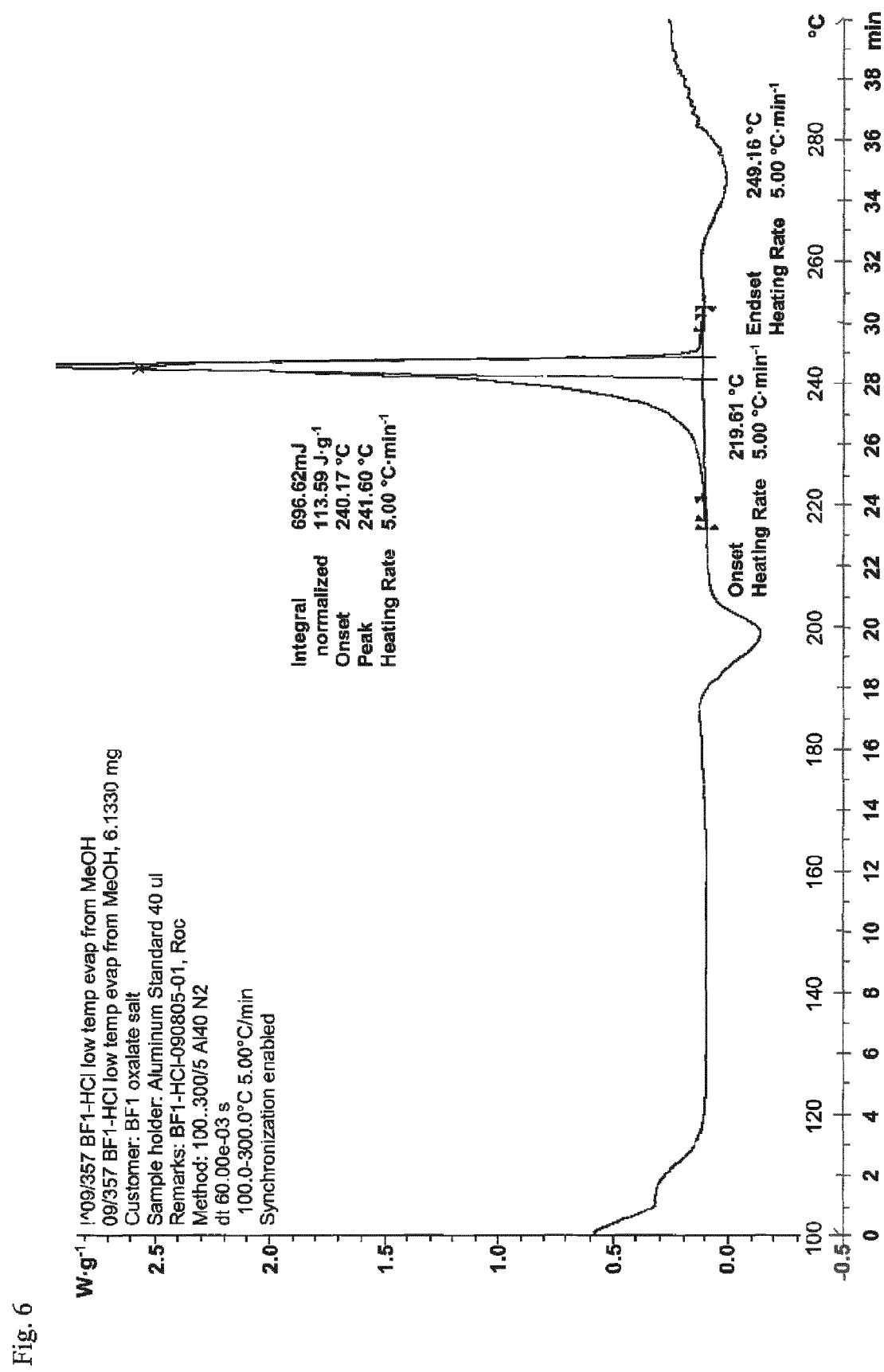
FIG. 6 shows a DSC analysis of crystals of 4-(6-ethoxy-1-methoxy-thioxanthene-9-ylidene)-1-methyl piperidine hydrochloride that were obtained by dissolving the starting material in MeOH and low temperature evaporation under reduced pressure.

| Sample Id | Method/Solvent | DSC Comparable with reference | XRPD Comparable with reference | Comment |
|---|---|---|---|---|
| 2 | Methanol cold evaporation | No* | No** | *minor exotherm at around 200° C., see FIG. 6 **XRPD pattern differs, see FIG. 3 |

TABLE 2-continued

Results from First Evaluation of Polymorphic Screening

Figure 4:
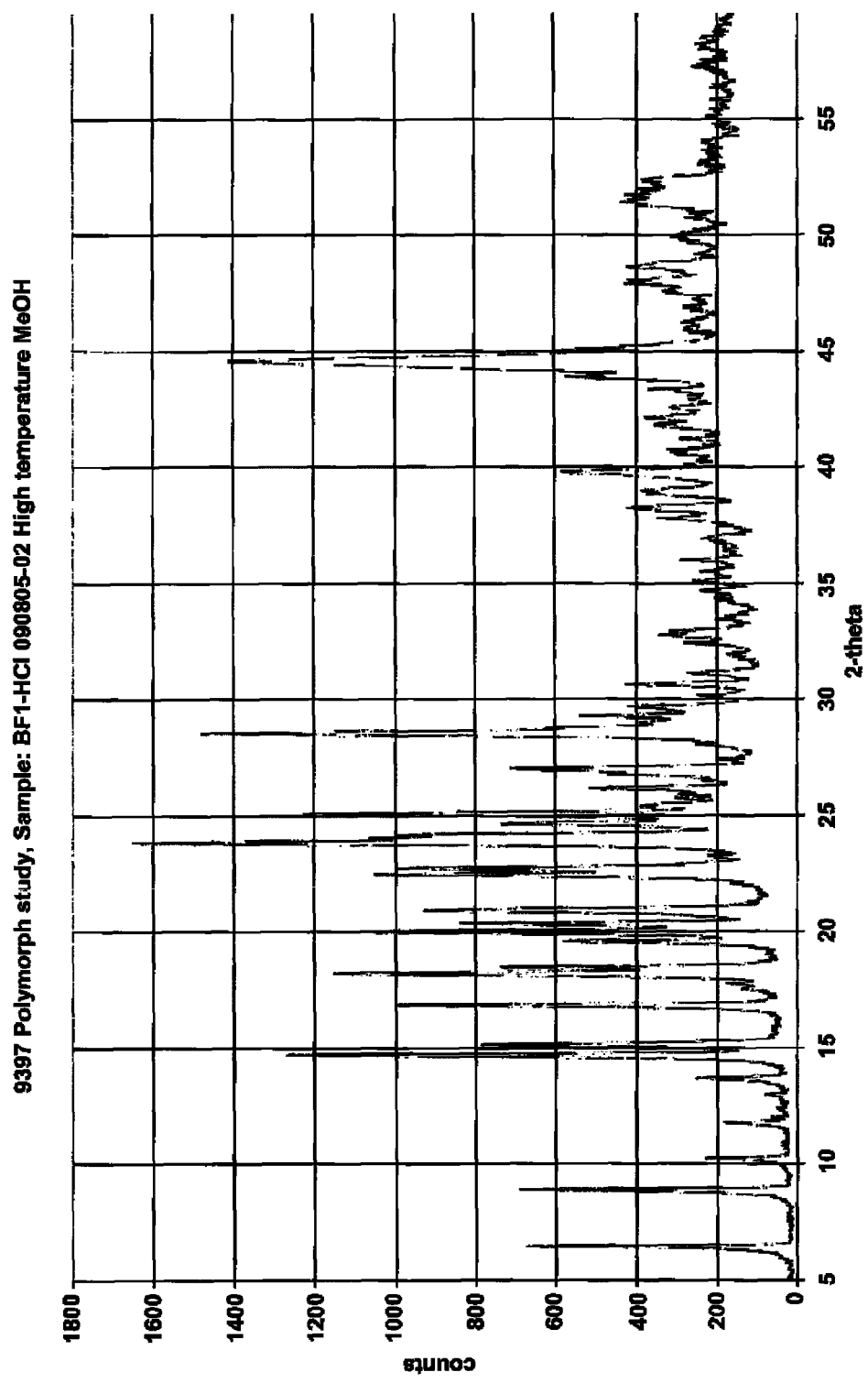
FIG. 4 shows an x-ray powder diffraction spectrum of crystals of 4-(6-ethoxy-1-methoxy-thioxanthene-9-ylidene)-1-methyl piperidine hydrochloride that were obtained by dissolving the starting material in MeOH and high temperature evaporation under normal pressure.
Figure 7:
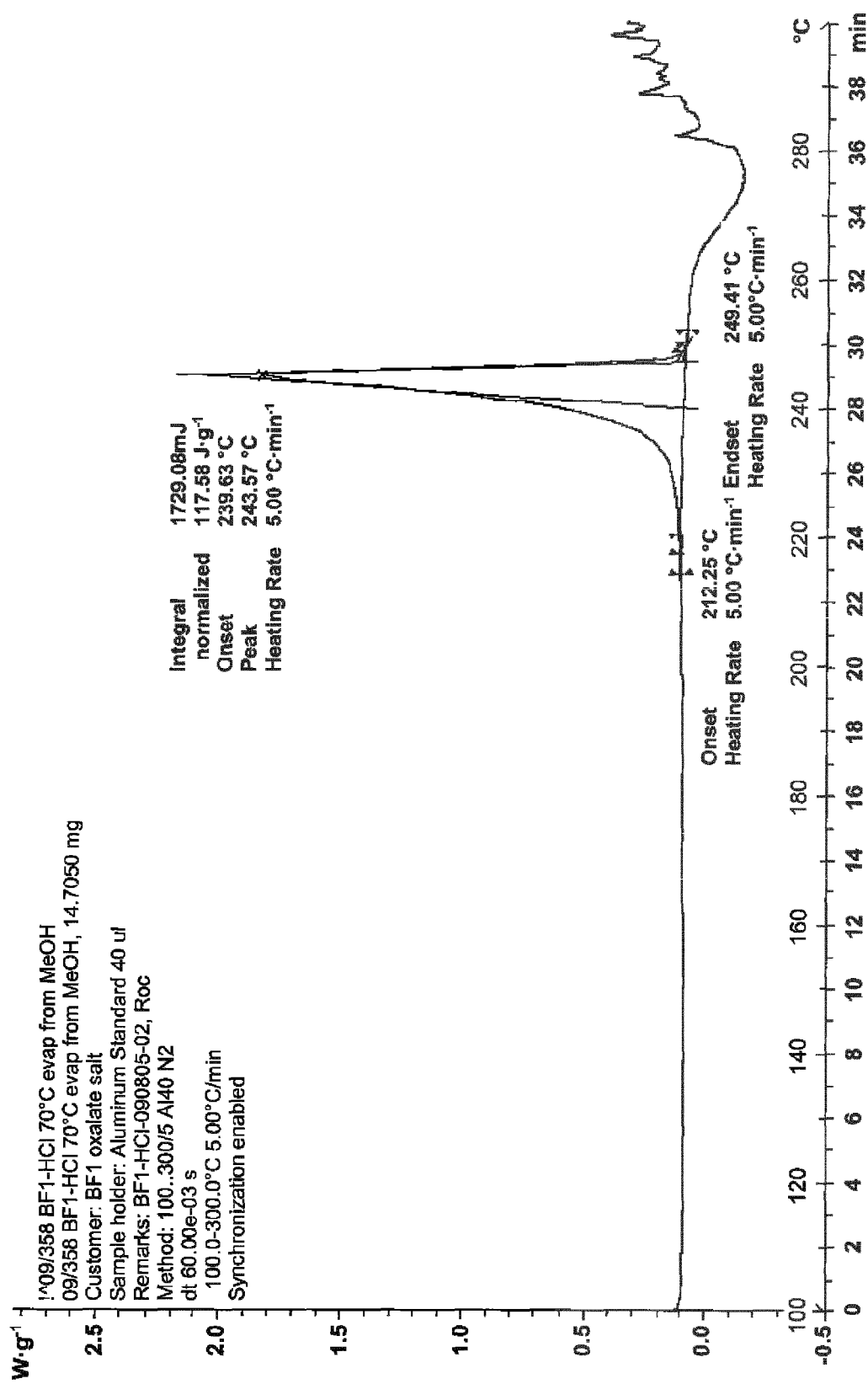
FIG. 7 shows a DSC analysis of crystals of 4-(6-ethoxy-1-methoxy-thioxanthene-9-ylidene)-1-methyl piperidine hydrochloride that were obtained by dissolving the starting material in MeOH and high temperature evaporation under normal pressure.

| Sample Id | Method/Solvent | DSC Comparable with reference | XRPD Comparable with reference | Comment |
|---|---|---|---|---|
| 3 | Methanol hot evaporation | Yes | Yes | Same morph as 1; see FIG. 4 and FIG. 7 |
| 4 | MeOH at 53° C., hot MTBE was added sol cooled to 10° C. | Yes | Yes | Same morph as 1; data not shown |
| 5 | MeOH at 53° C., hot EtOAc was added sol cooled to 10° C. | Yes | Yes | Same morph as 1; data not shown |
| 6 | MeOH at 53° C., hot acetone was added sol cooled to −20° C. | Yes | Yes | Same morph as 1; data not shown |

Sample 2, which was prepared by dissolving in methanol at room temperature and evaporating to dryness on an ice bath, does not appear to be the same crystalline form as the others. A comparison of the XRPD spectra of sample 2 (see FIG. 3) and the starting material (see FIG. 2) indicates that there appears to be amorphous content; the peaks are not nearly as distinct and there are other peaks which are non-existent in the other samples.

In addition, sample 2 is the only one where DSC shows a minor exotherm at around 200° C. (see FIG. 6). To confirm whether this is a second morph and which is the stable one, the sample was analysed for methanol by R (data not shown). Sample 2 does NOT contain any solvated methanol (which would indicate a pseudomorph).

It has also been confirmed that sample 2 has a higher solubility than the starting material. The starting HCl salt (sample Id 1) and the salt received from the low temperature evaporation (sample Id 2) were dissolved in 3 solvents with different capacities in solubility, namely methanol, 2-propanol and 96% ethanol (see Table 3 below). The solubility of sample Id 1 and sample Id 2 is shown in the rightmost column of Table 3 in mg/ml. The salt received from the low temperature evaporation (sample Id 2) exhibited an enhanced solubility in all three solvents tested in comparison to the starting material (sample Id 1). The increase in solubility ranged from about 9% (96% ethanol; (62−57)/57× 100%≈9%) to about 25% (in 2-propanol; (5−4)/4× 100%=25%).

TABLE 3

Comparison of Solubilities of Sample Id 1 and Id 2 in Three Different Solvents

| Sample | Solvent | Tara | Amount | After evap. | Weight-% | Weight of 200 µl | density | mg/ml |
|---|---|---|---|---|---|---|---|---|
| Starting Material | Methanol | 13311.6 | 274.3 | 13345.9 | 12.50% | 159.9 | 0.80 | 156 |
| Low. temp. evap. MeOH | Methanol | 13237.3 | 389.3 | 13287.6 | 12.92% | 150.9 | 0.75 | 171 |
| Starting Material | 2-Propanol | 13205.2 | 555.4 | 13206.7 | 0.27% | 151.5 | 0.76 | 4 |
| Low. temp. evap. MeOH | 2-Propanol | 13369.6 | 583.9 | 13371.8 | 0.38% | 150.7 | 0.75 | 5 |
| Starting Material | Ethanol 96% | 13150.8 | 519.3 | 13174.5 | 4.56% | 160.3 | 0.80 | 57 |
| Low. temp. evap. MeOH | Ethanol 96% | 13558.7 | 651.3 | 13589.3 | 4.70% | 152.2 | 0.76 | 62 |

It is a thermodynamic principle that the more stable morph does always have the lower solubility in any solvent at any temperature.

Furthermore, the identity and chemical structure is verified by the aid of infrared spectroscopy.

Figure 8:
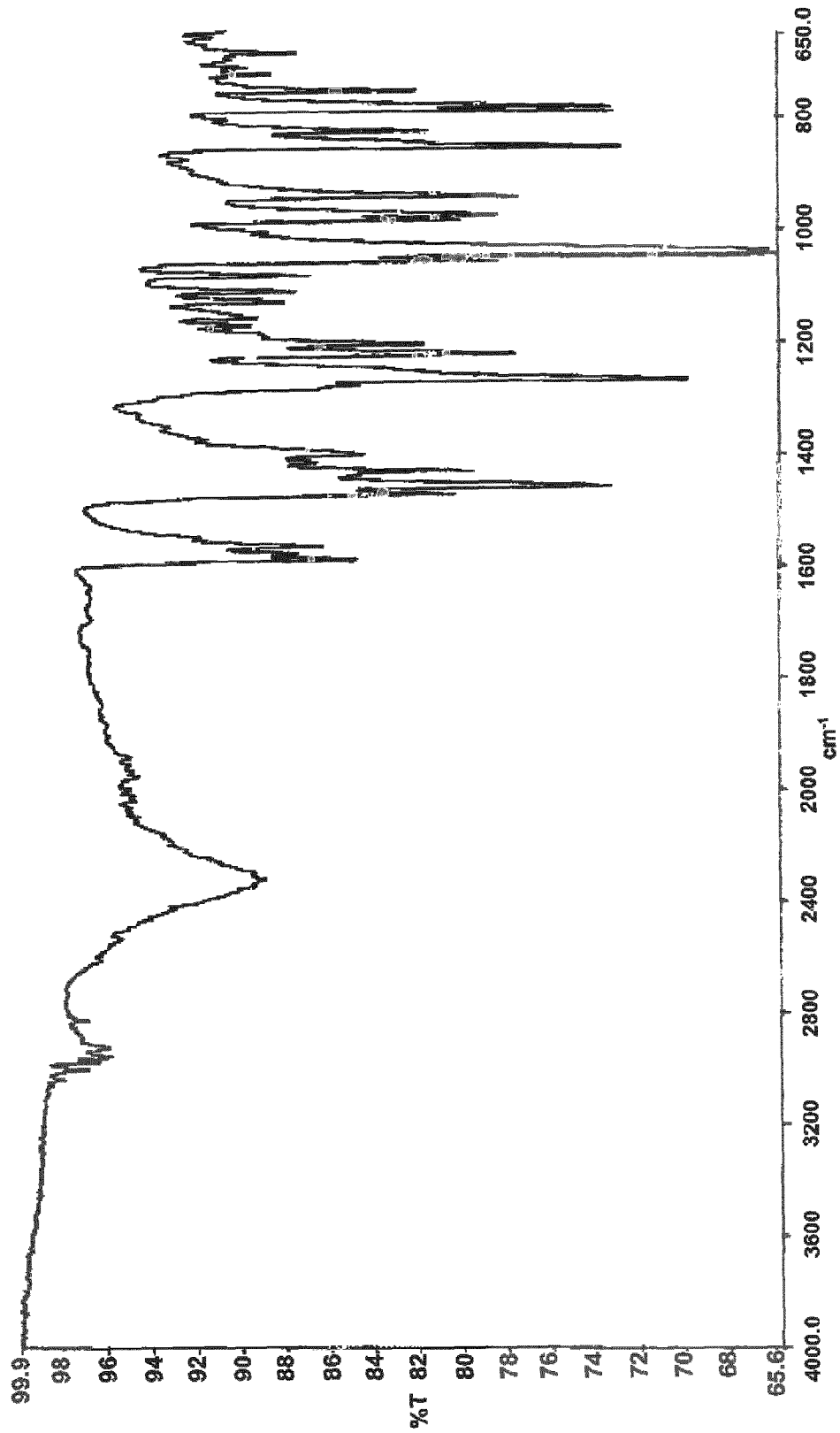
FIG. 8 shows an IR spectrum of crystals of 4-(6-ethoxy-1-methoxy-thioxanthene-9-ylidene)-1-methyl piperidine hydrochloride. The IR spectrum complies with the chemical structure of said salt.

The tentative signal assignments are given commented in Table 4. The IR spectrum provided in FIG. 8 below complies with the chemical structure of 4-(6-ethoxy-1-methoxy-thioxanthene-9-ylidene)-1-methyl piperidine hydrochloride.

TABLE 4

Tentative assignments of IR spectrum of 4-(6-ethoxy-1-methoxy-thioxanthene-9-ylidene)-1-methyl piperidine hydrochloride

| Band (cm-1) | Intensity | Comments |
|---|---|---|
| 775, 825 | Medium | Indicative of aromatics, 1,2,3 and 1,2,4-trisubstituted |
| 1050, 1250 | Strong | Aromatic aliphatic ether |
| 1400-1600 | Strong | Aromatic |
| 2400 | Medium (Broad) | Broad specific amine salt |

2.2 Second Evaluation

The solvent mix intended to be used in the final API crystallization was tested at different temperatures/order of addition:

7. 4-(6-ethoxy-1-methoxy-thioxanthene-9-ylidene)-1-methyl piperidine hydrochloride (3 g) was dissolved in 6 ml of MeOH at 53° C., thereafter the solution was added to 13.5 ml of warm MTBE and cooled to 10° C. No crystals were formed immediately after mixing the solutions. Some precipitate formed in solution and walls after cooling to room temperature (~15 min). Cooling to 10° C. over night without stirring caused formation of crust. The crust broke off during drying at 40° C. under vacuum. 2.7 g of crystals.

8. 4-(6-ethoxy-1-methoxy-thioxanthene-9-ylidene)-1-methyl piperidine hydrochloride (2 g) was dissolved in 20 ml MeOH at 20° C. The solution was added into 40 ml cold (10° C.) MTBE over 1 min. No crystals were formed immediately after mixing the solutions and during the initial cooling to 10° C. Loose crystals on the walls formed only after standing at 10° C. overnight. After drying the crystals at 40° C. under vacuum. 0.9 g of crystals obtained.

9. 4-(6-ethoxy-1-methoxy-thioxanthene-9-ylidene)-1-methyl piperidine hydrochloride (3 g) was dissolved in 6 ml MeOH at 53° C. Cold (~10° C.) MTBE 13.5 ml was added over 1 mm. No crystals were formed immediately after mixing the solutions. Cooling to 10° C. over night whithout stirring caused formation of crust. Remove the solution, wash the crystals with 5 ml MTBE. The crust broke off during drying at 40° C. under vacuum. 2.8 g of crystals.

TABLE 5

Results from Second Evaluation of Polymorphic Screening

| Sample Id | Method/Solvent | DSC Comparable with reference | XPPD Comparable with reference | Comment |
|---|---|---|---|---|
| 1 | Starting material | NA | NA | |
| 7 | MeOH sol 53° C., added into hot MTBE and cooled to 10° C. | Yes | Yes | Same morph as 1; data not shown |
| 8 | MeOH sol at 20° C. added into cold MTBE and cooled to 10° C. | Yes | Yes | Same morph as 1; data not shown |
| 9 | cold MTBE added to MeOH sol 53° C. and cooled to 10° C. | Yes | Yes | Same morph as 1; data not shown |

2.3 Conclusions

The above experiments show that 4-(6-ethoxy-1-methoxy-thioxanthene-9-ylidene)-1-methyl piperidine forms a stable addition salt with hydrogen chloride that can be obtained in high purity (>99%) and good yields (>60%).

The polymorphic screening shows that a morph made under kinetic conditions (sample 2) has higher solubility than the morph obtained under thermodynamic conditions (starting material and samples 1, 3, 4, 5, 6, 7, 8 and 9). Thus, it can be concluded that the morph obtained under the thermodynamic conditions is the most stable form of 4-(6-ethoxy-1-methoxy-thioxanthene-9-ylidene)-1-methyl piperidine hydrochloride. Without wishing to be bound by any particular theory, the present inventors expect that this stable form will be well-suited for preparing stable pharmaceutical formulations having long-term stability.

The invention claimed is:

1. A salt polymorph of 4-(6-ethoxy-1-methoxy-thioxanthene-9-ylidene)-1-methyl piperidine hydrochloride characterized by an x-ray powder diffraction spectrum having peaks expressed as 2 theta at about [14.7, 18.2, 20.0, 20.9, 22.5, 22.7, 23.8, 25.1, 28.6, 44.7] degrees using XRPD radiation.

2. The salt polymorph according to claim 1, which has a differential scanning calorimetry melting temperature maximum of from about 242 to about 244° C.

3. The salt polymorph according to claim 1, which has a differential scanning calorimetry heat of fusion of from about 90 to about 125 J/g.

4. The salt polymorph according to claim 1, which has a melting point of about 241° C.

5. The salt polymorph according to claim 1, which has major infrared absorbance peaks at about [775, 825, 1050, 1250, 1400-1600, 2400] $cm^{-1}$.

6. The salt polymorph according to claim 1, wherein the solubility in methanol is 156mg/ml.

7. The salt polymorph according to claim 1, wherein the solubility in 2-propanol is 4mg/ml.

8. A method of forming a salt polymorph according to claim 1, the method comprising:
   (a) dissolving a 4-(6-ethoxy-1-methoxy-thioxanthene-9-ylidene)-1-methyl piperidine hydrochloride addition salt in a protic solvent, wherein said protic solvent is methanol, and
   (b) removing said protic solvent at a temperature above 40° C.

9. The method according to claim 8, wherein the removing of said protic solvent in step (b) is carried out at a pressure above $5 \times 10^4$ Pa.

10. The method according to claim 8, wherein the temperature in step (b) is in the range of 50 to 80° C.

11. The method according to claim 9, wherein the removing of said solvent in step (b) is carried out at a pressure above $1 \times 10^5$ Pa.

12. A method for treating migraine or pulmonary hypertension comprising the step of administering the salt polymorph according to claim 1 or 4-(6-ethoxy-1-methoxy-thioxanthene-9-ylidene)-1-methyl piperidine hydrochloride addition salt or 4-(6-ethoxy-1-hydroxy-thioxanthene-9-ylidene)-1-methyl piperidine hydrochloride addition to a subject in need thereof.

13. A method for treating migraine or pulmonary hypertension comprising the step of administering a pharmaceutical composition comprising the salt polymorph according to claim 1 or 4-(6-ethoxy-1-methoxy-thioxanthene-9-ylidene)-1-methyl piperidine hydrochloride addition salt or 4-(6-ethoxy-1-hydroxy-thioxanthene-9-ylidene)-1-methyl piperidine hydrochloride addition salt and one or more pharmaceutical excipients or additives to a subject in need thereof.

14. The method according to claim 13, wherein the pharmaceutical composition is administered orally, rectally, intragastrically, intracranially or parenterally.

15. The method according to claim 14, wherein the parenteral administration of the pharmaceutical composition is selected from the group consisting of intravenous, intramuscular, intranasal, intradermal, and subcutaneous administration.

* * * * *